US006830655B2

United States Patent
Siika-Aho et al.

(10) Patent No.: US 6,830,655 B2
(45) Date of Patent: Dec. 14, 2004

(54) METHOD OF MODIFYING A XYLAN-CONTAINING CARBOHYDRATE SUBSTRATE HAVING HEXENURONIC ACID GROUPS ATTACHED TO THE XYLAN

(75) Inventors: Matti Siika-Aho, Helsinki (FI); Johanna Buchert, Espoo (FI); Tapani Vuorinen, Espoo (FI); Anita Teleman, Espoo (FI); Maija Tenkanen, Espoo (FI); Michael Bailey, Espoo (FI); Liisa Viikari, Helsinki (FI)

(73) Assignee: Valtion Teknillinen Tutkimuskeskus, Espoo (FI)

( * ) Notice: Subject to any disclaimer, the term of this patent is extended or adjusted under 35 U.S.C. 154(b) by 0 days.

(21) Appl. No.: 08/750,069

(22) PCT Filed: Jun. 5, 1995

(86) PCT No.: PCT/FI95/00317

§ 371 (c)(1),
(2), (4) Date: Feb. 6, 1997

(87) PCT Pub. No.: WO95/33883

PCT Pub. Date: Dec. 14, 1995

(65) Prior Publication Data

US 2004/0069426 A1 Apr. 15, 2004

(30) Foreign Application Priority Data

Jun. 3, 1994 (FI) .................................................. 942639

(51) Int. Cl.$^7$ .............................................. D21H 25/02
(52) U.S. Cl. .......................... 162/72; 435/277; 435/278; 435/814
(58) Field of Search ............................ 162/72; 435/277, 435/278, 814

(56) References Cited

U.S. PATENT DOCUMENTS 4,200,692 A * 4/1980 Puls et al. .................. 435/814

OTHER PUBLICATIONS

NOVO Brochure, Pulpzyme HA, Sep. 1989.*
Pedersen, "On the Use of Pulpzyme HA for Bleach Boosting", Novo–Nordisk, Sep. 1989.*

* cited by examiner

Primary Examiner—Steve Alvo
(74) Attorney, Agent, or Firm—Kubovcik & Kubovcik

(57) ABSTRACT

The present invention concerns a method for enzymatic treatment of lignocellulosic materials which contain xylan-polymers, such as cellulose kraft pulps. According to a method of the present kind, at least a part of the hexenuronic acid groups present in the material is selectively removed in order to remove metal ions from the pulp, to change the surface charge thereof, to improve the brightness stability of the pulp and to render the material more suitable for enzymatic treatment.

14 Claims, 1 Drawing Sheet

Conversion of methyl glucuronic acids into hexenuronic acids during cooking

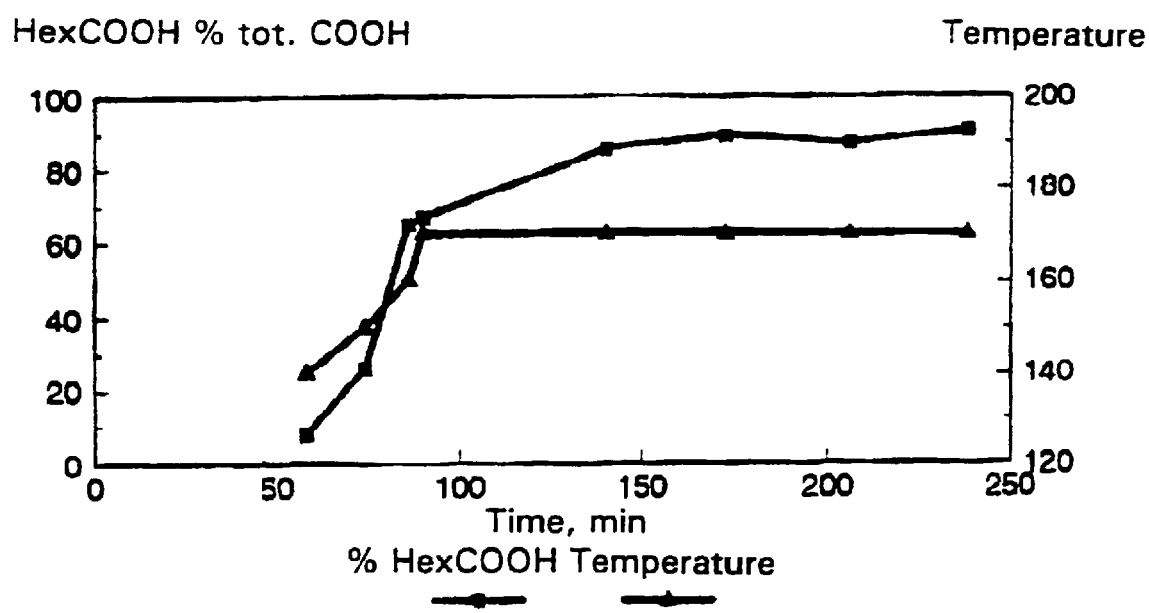
Conversion of methyl glucuronic acids into hexenuronic acids during cooking

METHOD OF MODIFYING A XYLAN-CONTAINING CARBOHYDRATE SUBSTRATE HAVING HEXENURONIC ACID GROUPS ATTACHED TO THE XYLAN

FIELD OF THE INVENTION

The present invention concerns a method in accordance with the preamble of claim 1 for treatment of cellulose pulps, in particular pulps prepared by the kraft process and by extended pulping processes.

The invention also concerns an enzymatic preparation according to the preamble of claim 17 as well as a method for isolating enzyme-producing strains and a method for producing a desired enzyme.

BACKGROUND OF THE INVENTION

In traditional chlorine bleaching the residual lignin of cellulose pulps is solubilized by using chlorine or chlorine dioxide. Presently the pulps are frequently also bleached by oxygen gas, hydrogen peroxide, ozone or by combined sequences including these substances as well as the above-mentioned traditional bleaching chemicals. Enzymatic treatments, carried out by hemicellulases or lignin degrading enzymes, have been combined with the traditional and new bleaching sequences leading to increased bleachability of the fibres. The amounts of enzymes needed to achieve the improved bleachability are low, and the enzymatic treatment can easily be incorporated into the pulp production processes.

Conventionally, the enzymatic treatments have been performed directly on fibres from the pulping processes. In an earlier PCT patent application, published under number WO 93/11296, we have shown that the properties of the cellulosic fibres profoundly affect the possibilities of enzymes to act efficiently on the pulps. Thus, for instance, the action of the xylanases is not optimal when the surface charge, i.e. the zeta potential, is very low. Furthermore, a kraft pulp treated at a low pH-value, at which the carboxylic groups of the hemicelluloses present in the pulp are in an acid form (and do not contain metal counter ions), constitutes a rather poor substrate for enzymatic (hemicellulase) treatments. By enzymatically removing the carboxylic groups of the hemicelluloses from the cellulose pulps, both the surface charge and the metal-ion content of the pulp can be changed. According to a method of our earlier patent application, the methyl glucuronic acid groups, can be removed by treating the cellulose pulp with an enzyme preparation having an essential glucuronidase enzyme activity. That activity will cleave the bond between the xylose unit of the xylan chain and the carboxylic acid side group, whereby the carboxylic group will be removed.

Although quite promising results have been obtained with the glucuronidase enzyme treatment, there is still a need for further improving the modification of pulps, in particular kraft pulps and some modified (extended) cooking pulps, containing very small amounts of glucuronic acids.

SUMMARY OF THE INVENTION

In connection with the present invention it has surprisingly been found that the acidic side chains of pulp xylan are not exclusively composed of 4-O-methyl-α-D-glucuronic acid or α-D-glucuronic acid, as presently believed, but during pulping by the conventional kraft method as well as by some of the new, extended cooking methods an essential part of the 4-methyl glucuronic acid (in the following shortened MeGluA) is in fact converted to an unsaturated derivate thereof, viz. 4-deoxy-α-L-threo-4hexenuronic acid, or hexenuronic acid, (HexA). This carboxylic acid group can, depending on the aching conditions, also be found in the bleached pulp.

With reference to the above findings, the present invention provides a novel solution for modification of industrial pulps, which is based on the concept of selectively removing at least a part of the hexenuronic acid groups contained in the pulp.

In particular, the method according to the present invention is characterized by what is stated in the characterizing part of claim 1.

The enzyme preparation according to the present invention is characterized by what is stated in the characterizing part of claim 17. The method for isolating microorganism strains producing hexenuronidase activity is characterized by what is stated in the characterizing part of claim 22 and the method for producing hexenuronidase by what is stated in the characterizing part of claim 24.

DEFINITIONS

For the purpose of the present invention the term "glucuronic acid groups" is used as an abbreviation of 4-O-methyl-α-D-glucuronic acid or α-D-glucuronic acid groups. "Hexenuronic acid groups" is an abbreviation of 4deoxy-α-L-threo-4-hexenuronic acid groups.

The term "enzyme preparation" denotes any product which contains at least one enzyme. Thus, such an enzyme preparation may be a culture liquor containing one or more enzymes, an isolated enzyme or a mixture of one or more enzymes. In addition to the enzymatic activity such a preparation preferably contains adjuvants which commonly are used in enzyme preparations intended for application in the paper and pulp industry. Such adjuvants are typically comprised of, for instance, buffering agents and stabilizing agents.

The term "hexenuronidase" as used herein, refers to an enzyme which is capable of removing hexenuronic acid groups which are attached to xylose units. Similarly, "glucuronidase" is an enzyme capable of removing glucuronic acid groups attached to xylose units. The action of the hexenuronidase can be based on hydrolytic action, which cleaves the bond between the acid groups and the xylose units. Alternatively, the hexenuronidase can act on the unsaturated HexA ring, in particular the double bond thereof, destabilizing or breaking up the structure.

The term "uronidaes" covers both hexenuronidase and glucuronidase.

"A substantial amount of hexenuronidase" or "substantial amount of glucuronidase" indicates that the hexenuronidase and glucuronidase activities of the enzyme preparation are comparatively high, i.e. that the amounts are sufficient to release the uronic acid groups from the xylose units. In particular, the uronidase activities of the enzyme preparation should be so high that a substantial part of the uronic acid groups of the substrate can be removed by contacting the substrate with the enzyme.

"Kraft pulping" is used synonymously with "sulphate cooking" and it designates the cooking method in which sodium sulphide and sodium hydroxide are used as principal cooking chemicals. "New" or "modified" cooking methods are represented by pulping methods which are based on continuing the conventional kraft cooking until the Kappa number of the lignocellulosic material is reduced to below about 20. These methods typically include an oxygen treatment.

BRIEF DESCRIPTION OF THE DRAWING

The FIGURE shows the conversion of methyl glucuronic acid groups into hexenuronic acid groups as a function of pulping (pulp cooking) time.

DETAILED DESCRIPTION OF THE INVENTION

The various features and benefits of the present invention will be described in greater detail in the following description and in the working examples.

Evidence of the existence of hexenuronic acid groups

We have shown the existence of hexenuronic acid groups by hydrolysing with xylanase the polymeric xylan in kraft cooking pulp from pine, separating the acid oligosaccharides from the neutral ones and analysing the acid oligosaccharides with $^1H$ and $^{13}C$ NMR.

The procedure used is described in more detail in working examples 1 and 2.

According to observed NMR connectivities with the NOESY and HMBC methods, it is concluded that hexenuronic acid is attached $\alpha$-(1→2) to an internal xylose.

We have further found that after conventional kraft pulping, of the carboxylic groups of xylan, some 65% are made up of hexenuronic acid in the case of birch kraft pulp and some 80% in the case of pine kraft pulp. Some of the new cooking methods, in particular EMCC, MCC/$O_2$ and continuous pulping combined with oxygen treatment, produce pulps, wherein the carboxylic groups are almost exclusively comprised of hexenuronic acids. Thus, the FIGURE shows experimental results indicating the conversion of methyl glucuronic acids to hexenuronic acids during kraft pulping. It appears that the longer the cooking time, the larger part of the carboxylic groups is made up of hexenuronic acid groups. Table 1 contains data on the HexA and MeGlcA contents of various pulps.

TABLE 1

Composition of xylans of some industrial softwood pulps calculated from hydrolysates obtained from treatment with pulps by pI 9.0 xylanase of *T. reesei*

| Pulping method | Kappa (SCAN) | Xylose (% of d.w.) | MeGlcA (mol-%) | HexA (mol-%) |
|---|---|---|---|---|
| Extended batch + AQ | 13.10 | 6.3 | nd | 0.8 |
| EMCC | 18.90 | 6.8 | nd | 2.8 |
| Batch | 26.80 | 8.5 | 0.4 | 4.4 |
| Super-batch/$O_2$ | 6.40 | 5.6 | nd | 0.4 |
| MCC/$O_2$ | 11.80 | 8.3 | nd | 4.4 |
| Continuous/$O_2$ | 20.30 | 8.8 | nd | 5.5 |

AQ = Antraquinone
EMCC = Extended modified continuous cook
nd = not detected

The acid hydrolysis carried out in connection with traditional carbohydrate analysis destroys the hexenuronic acid, which to some extent explains why said acid has not been detected before in connection with routine carbohydrate analysis.

Further findings in connection with the present invention show that the relative amounts of the two types of uronic acids in bleached pulp depend on the bleaching conditions, as shown in Table 2.

TABLE 2

The influence of bleaching on the composition of surface xylan of pine kraft pulp (Kappa 25.9

| Bleaching sequence | Brightness | HexA (mol-%) | MeGluA (mol-%) | Ara (mol-%) | Xyl (mol-%) |
|---|---|---|---|---|---|
| Q | nd | 4.8 | 0.9 | 7.5 | 86.8 |
| QO | 49.8 | 4.8 | 1.0 | 7.5 | 86.6 |
| QOQZ | 62.5 | 1.3 | 1.0 | 7.6 | 90.1 |
| QOQZE | 63.8 | 1.6 | 1.0 | 7.9 | 89.6 |
| QOQZEP | 80.4 | 1.6 | 1.1 | 7.8 | 89.5 |
| QOQP | 75.5 | 4.7 | 1.1 | 7.4 | 86.8 |
| QOQPZ | 80.4 | 0.3 | 1.2 | 7.4 | 91.9 |
| QOQPZE | 80.8 | 0.2 | 1.1 | 7.4 | 91.3 |
| QOQPZEP | 88.5 | 0.3 | 1.3 | 7.6 | 90.8 |
| QOQPPP | 82.2 | 4.5 | 1.2 | 7.3 | 87.0 |
| QOQDEDED | 88.1 | 0.0 | 1.2 | 7.5 | 90.8 |

Q = EDTA treatment. O = oxygen. P = peroxide, E = alkaline extraction, D = chloride dioxide.

Thus, as apparent from the above data, in case of bleaching using peroxide or oxygen, hexenuronic acid makes up the bulk of the acidic side chains of the xylan. Oxidation by, e.g., chlorine dioxide or ozone during bleaching destroys the hexenuronic acid.

Isolation of hexenuronidase-producing strains and production of the enzyme

According to the present invention, at least a part of the hexenuronic acid groups is selectively removed from pulp. This selective removal can be effected enzymatically by using hexenuronidase or chemically by using agents which will selectively react with the double bond without substantially affecting the rest of the molecule. It is preferred to use hexenuronidase.

The present invention therefore also discloses a method of isolating microbial strains capable of producing hexenuronidase. In summary it comprises the steps of collecting samples of microorganism-containing organic matter from a pulp mill or the vicinity thereof or any other potential source containing material with this carbohydrate structure, suspending the samples in a suitable liquid or buffer, e.g. in a physiological salt solution, inocculating media containing as a carbon source oligomers containing hexenuronic acid with aliquots of the diluted suspension or directly the material collected as described before, incubating the inocculated medium in a suitable container, e.g. shake flask or fermentor, in conditions which favour microbial growth, until more than appr. 50% of the carbon source containing HexA is consumed, collecting the microbial cells from the cultivation liquid optionally repeating the cultivation, and optionally purifying the colonies or storing the possible mixed microbial population using standard microbiological methods.

The growth medium contains oligomers or xylan with hexenuronic acid together with suitable nitrogen sources. The method is illustrated in more detail in Examples 5 and 6.

Hexenuronidase can, be produced with a microbial strain or mixed microbial populations isolated according to the above method by cultivating the microorganism on growth media containing oligomers containing hexenuronic acid or xylan.

According to one preferred embodiment of the invention, the enzyme preparation used comprises the cultivation liquid or medium or intracellular extract, or solubilized intracellular enzymes of an uronidase-producing microorganism, isolated as described above. Preferably, such a cultivation medium or extract is concentrated before use. According to another preferred embodiment, the enzyme preparation comprises a purified enzyme, isolated from a cultivation liquid or from an intracellular extract.

The enzyme preparation useful for treatment of lignocellulosic materials comprises an essential uronidase enzyme activity and contains only minor amounts, if any, of hemicellulases (xylanases).

The invention is not, however, limited to the indicated origins of the enzyme nor to the isolation method, and the enzyme can also be obtained by other methods.

Thus, it is possible to produce the uronidase enzyme by microorganisms, which have been mutated or genetically constructed to produce the desired enzyme, or by other production host strains, to which the gene encoding this enzyme has been transfered.

The uronidase preparation can be derived from a microorganism strain selected from the group essentially consisting of microorganisms of the genera *Trichoderma* (e.g. *T. reesei. T. harzianum*), *Aspergillus* (e.g. *A. niger, A. awamori, A. terreus, A. oryzae*), *Schizophyllum* (e.g. *S. commune*), *Aureobasidium* (e.g. *A. pullulans*), *Phanerochaete* (e.g. *P. chrysosporium*), *Fusarium* (e.g. *F. oxysporum*), *Agaricus* (e.g. *A. bisporus*), *Penicillium* (e.g. *P. janthinellum, P. digitatum*), *Streptomyces* (e.g. *S. olivochromogenes, S. flavogriseus*), *Bacillus* (e.g. *B. subtilis, B. circulans*), and *Xanthobacter* (e.g. *X. autotrophicus*). It can also be derived from a microorganism strain selected from the group comprising *Thermoascus auranticus, Curvularia inequalis, Tyromyces palustris, Cryptonectria parasitica, Myceliophthora thermophila*, and *Thermobacter auranticus*. Microorganisms producing xantanase and pectinase can also be used.

Especially suitable are also strains, isolated from pulp mill sites, which are capable of degrading xylans containing HexA.

All these microorganisms can be used to produce uronidases, which are able to remove the uronic side groups (HexA or MeGlcA) of xylan.

According to a preferred embodiment, the enzyme preparations are prepared by cultivating on a cultivation medium comprising xylans or compounds containing hexenuronic acid groups any of the above-mentioned uronidase-producing microorganisms.

The present enzyme preparations typically contain suitable adjuvents such as buffering agents, conventionally used in enzyme preparations intended for use on pulp and paper.

INDUSTRIAL APPLICABILITY

The present invention is based on the concept of selectively removing the hexenuronic acid groups from a xylan-containing carbohydrate substrate. In contrast to the above-mentioned strong oxidation methods which not only destroy the hexenuronic acid groups but also affect the chemical structure of the whole carbohydrate part of the material, selective removal is required according to the invention.

In cases where the xylan contains both HexA and MeGlcA, it is generally desirable specifically to remove at least partially both side groups. Preferably, the uronic groups are removed enzymatically by contacting the substrate with the corresponding enzyme, i.e. hexenuronidase or glucuronidase, respectively.

According to the method of the present invention, the technical properties, e.g. brightness stability, of paper prepared from the pulps can be modified by enzymatically removing the carboxylic groups of the pulps in particular from the surface of the pulp fibres (cf. Example 12). In particular the present invention can be applied to cellulose pulps prepared by kraft pulping or modified (kraft) pulping, as mentioned above. This is demonstrated in Example 8, wherein by removing only part of the HexA-groups, the brightness stability of the pulp was markedly improved.

According to one preferred embodiment, the hexenuronic acid groups are removed before the bleaching stage of cellulose pulp. As evident from the data in Table 2, there are considerable amounts of hexenuronic acid groups present in peroxide or oxygen bleached TCF pulps. By removing these (and other) carboxylic groups from the pulps, metal cations contained therein are also removed. Thus, the consumption of bleaching chemicals, in particular complexing agents such as EDTA or DTPA, can be decreased. Because the treatment according to the invention decreases the metal-ion content of pulps, hydrogen peroxide or oxygen can be advantageously used as the bleaching chemical.

According to another prefered embodiment, the amounts of carboxylic groups in the pulp are modified by using hexenuronidase in such a way that the action of hemicellulases or other enzymes on fibre materials can be optimized and enhanced essentially without unnecessary degradation of the hemicelluloses in the fibres. The higher the relative hexenuronidase activity of the enzyme preparation is, the easier it is to reach this goal. Thus, the bleachability of TCF-pulps (totally chlorine free pulps) can be increased by treatment(s) with uronidase(s).

The hexenuronidase treatment can be conducted separately, simultaneously with another enzymatic treatment, or before such a treatment. It is particularly preferred to combine the hexenuronidase treatment with a glucuronidase treatment. When the hexenuronidase treatment is carried out simultaneously with a hemicellulase treatment carried out by using xylanase or mannanase, for instance, it is preferred to use an enzyme preparation to which the uronidase has been added, or which has been produced by a strain genetically improved to produce high uronidase activity, in order to obtain a preparation with an essentially high uronidase activity. According to the invention, the hexenuronidase treatment can also be combined with treatments with cellulases and/or lignin modifying activities. As examples of the latter enzymes, lignin peroxidase, laccase and Mn-dependent peroxidase can be mentioned.

In addition to chemical pulps, the method of the invention is also suitable for the treatment of any lignocellulosic pulps, i.e. mechanical or chemimechanical pulps. Thus, in our studies, we have unexpectedly found out that the brightness reversion of pulps can be decreased by removing enzymatically methyl glucuronic acid or hexenuronic acid groups.

BENEFITS OF THE INVENTION

The method according to the invention provides remarkable advantages. The effect of the treatment is based specifically on the removal of charged groups and not on the total hydrolysis of hemicelluloses. The effect of the present method is based on the enzymatic removal of uronic acid groups in order to change the surface charge into an advantageous form with respect to further treatment either chemical or enzymatical. By changing the described factors (such as surface charge) the action of, e.g., enzymes to affect the most advantageous parts of the fibre substrate can be regulated. The invention makes it possible directly to affect the type and amount of chemicals to be used for the industrial scale extraction of lignin from the fibres and can be further used to improve the low-chlorine or chlorine-free bleaching methods, thus reducing environmental pollution.

The present invention provides for removal of carboxylic groups from pulps which do not contain any significant amounts of methyl glucuronic acid groups.

By treating pulp with a uronidase as described herein prior to or simultaneously with the treatment of the pulp with another enzyme (e.g. xylanase), the do of enzymatic hydrolysis can be increased, in particular in the case when metal-free pulp is used as a substrate.

By treating the pulp with a uronidase enzyme the metal binding uronic acid groups can be removed which will decrease the amount of the metal-ions in the pulp. Hence the use of complexing agents (for instance EDTA or DTPA) prior to TCF bleaching can be reduced or totally omitted.

The enzymatic removal of glucuronic acid groups can be used to improve the production of certain pulps, such as metal-free pulps or pulps with very low amounts of carboxyl groups.

It is also typical for the method of invention that the technical properties of paper manufactured from the chemical and mechanical pulps can be modified.

WORKING EXAMPLES

The method of invention is described in the following by some non-limiting examples. Details on the production of α-glucuronidase which can be used together with the hexenuronidase are given in our previous PCT Application (WO 93/11296).

As mentioned above, the number of carboxylic groups and of counter-ions bound to them affect the electric charge of the pulp. These factors can be described by different chemical and physical parameters and the surface charge of fibres (pulps) can be measured with the zeta-potential (Melzer 1972). The metal content of pulps can be measured by analyzing the metals in pulp with an atom absorption spectrophotometer. The carboxylic acid content of pulps can be measured e.g. by the method of Sjöström (KCL method 192:68). The action of enzymes in the fibres can be described by the liberation of sugars and by the extractability of lignin fragments after the enzymatic treatment.

Example 1

Preparation of Oligosaccharides Containing Hexenuronic Acid (HexA)

Birch kraft pulp with kappa number of 17–18 was obtained from Kaukas pulp mill. First the composition of the pulp was analysed as follows to confirm that the content of hexenuronic acid in the pulp was adequate. The pulp was treated by xylanase (pI 9) of *T. reesei* at 40° C. for 24 h, resulting in solubilization of 27% of pulp xylan. The consistency of the pulp in the hydrolysis was 5%, enzyme dosage was 10,000 nkat/g pulp and the pH was adjusted to pH 5.0 by sulphuric acid. After the hydrolysis the sample was filtrated, boiled and lyophilized. The lyophilizate was analysed by NMR. The sugar constituents of the hydrolysate were:

| | |
|---|---|
| xylose units | 95% |
| hexenuronic acid | 4.2% (bound to xylose units) |
| methyl glucuronic acid | 0.8% (bound to xylose units) |

To release oligomeric HexA-containing oligomers 223 kg of the wet pulp was gradually added in 400 l of water during the first 24 hours of enzyme treatment and hydrolysed with commercial cellulase (Econase, Oy Alko Ab) and xylanase (Ecopulp, Oy Alko Ab) preparations. The enzyme dosages derived from both preparations were: 6200 nkat/g dry pulp endoglucanase (assayed as activity against hydroxy ethyl cellulose, IUPAC, 1989) and 10500 nkat/g dry pulp xylanase (assayed by the method of Bailey at al., 1992). The hydrolysis conditions were: temperature 40–45° C., pH 5 and duration 3 days. Hydrolysis was terminated by boiling for 15 min. After cooling the hydrolysate was held with mild agitation at +5° C. overnight.

The hydrolysate was clarified by pressure filtration in a Seitz Orion C-40 plate and frame filter. Before filtration 3.5 kg of filter aid (diatomaceous earth, Celite Standard Super-Cel) was added to the hydrolysate. About 600 l of clear filtrate was obtained in 20 min. The acidic hydrolysis products in the hydrolysate were analysed by high performance anion exchange chromatography coupled with pulsed amperometric detection (Dionex Corp.) The acidic constituents identified were: methyl glucuronic acid 390 mg/l, glucuronic acid 98 mg/l and three oligomers substituted by hexenuronic acid ($HexAX_2$, $HexAX_3$ and an unknown oligomer marked as $HexAX_{n3}$) in concentrations of:

| | |
|---|---|
| $HexAX_1$ | ca. 800 mg/l |
| $HexAX_2$ | ca. 1100 mg/l |
| $HexAX_3$ | 20 U/l, | where 1 U corresponds to the response of 1.0 in the detector signal.

The structure of the major components containing hexenuronic acid was confirmed by NMR. These compounds included a hexenuronic acid unit attached to the non-reducing end of xylobiose in the smaller and to the non-reducing end of xylotriose in the larger oligosaccharide.

The hydrolysate was applied in 10 batches of 50 l on an anion exchanger (Dowex 1×2, 100–200 mesh, Cl⁻ form, 2.2 kg), packed in a 6 l column (BP-252, Pharmacia). The flowrate was approximately 450 ml/min, and the eluents used were:

1. 1 M NaAc (for regeneration of the gel),
2. distilled water (for equilibration prior to sample application)
3. sample application,
4. distilled water (for washing the column),
5. 0.1 M NaAc (for elution of the acidic products at lower ionic strength) and
6. 1 M NaAc (for elution at higher ionic strength and regeneration of the gel).

Fractions of 450 ml or 900 ml were collected and analysed. All the ten cycles were equivalent as judged by conductivity and UV-absorbance measurements from the eluted fractions. No acidic oligomers were detected in the non-adsorbed material.

The peak fractions from 4 cycles were pooled and lyophilized. The compositions of these pools are given in the following table.

TABLE 3

Composition of pooled fractions

| Preparate | Volume l | Dry matter % | HexAX$_{n1}$ + HexAX$_{n2}$ + HexAX$_{n3}$ U/ml(*) | HexAX$_{n1}$ + HexAX$_{n2}$ + HexAX$_{n3}$ 1000 U(*) | MeGlcA mg/l | MeGlcA g | GlcA mg/l | GlcA g |
|---|---|---|---|---|---|---|---|---|
| A (low salt) | 3.9 | 1.65 | 2900 | 11 | 200 | 0.78 | 50 | 0.20 |
| B (high salt) | 3.5 | 7.4 | 7800 | 27 | 6800 | 24 | 700 | 2.5 |
| C (low salt) | 3.8 | 1.93 | 3600 | 14 | 580 | 2.2 | 50 | 0.19 |
| D (high salt) | 3.8 | 7.4 | 8800 | 33 | 7600 | 29 | 640 | 2.4 |

(*) 1 U is equivalent to approximately 3 mg of oligomers (1 U corresponds to the response of appr. 1.0 in the detector signal).

1 g of lyophilized preparation P-229 B-C II was dissolved in 10 ml of dist. water. The sample was applied to a column of Bio-Gel P-2 (Bio-Rad, height 90 cm, volume 1.8 l) previously equilibrated with distilled water. Fractions of 15 ml were collected during the elution by distilled water. The fractions containing the highest concentration of HexAX$_2$ were pooled and concentrated to 10 ml by evaporation. After this, similar gel filtration runs were repeated two times. The peak fraction of the third gel filtration contained more than 90% of HexAX$_2$ as judged by chromatographic analysis and confirmed by NMR.

To obtain a crude fraction of oligomers with a low acetate content, 20 g of lyophilized preparation P-229 B-C II was dissolved in 60 ml of distilled water. The sample was applied to a column of Sephadex G-10 (Pharmacia, height 55 cm, volume 1.1 l) previously equilibrated with distilled water. Fractions of 15 ml were collected during the elution by distilled water. The fractions having the highest concentration of oligomers containing hexenuronic acid were pooled. The pool collected contained ca. 5 g of these oligomers. Large batches of desalted material with the oligomers containing hexenuronic acid could be prepared by repeating the run several times.

References

Bailey, M. J., Biely, P. and Poutanen, K. (1992) Interlaboratory testing of methods for assay of xylanase activity. J. Biotechnol. 23, 257–270

IUPAC (International Union of Pure and Applied Chemistry) (1989) Measurement of cellulase activities. Pure Appl. Chem. 59. 257–268.

Example 2
Preparation of Xylan Containing Hexenuronic Acid (HexA)

Glucuronoxylan (Roth 7500, 7.5 g) was treated with sodium borohydride (100 mg) in alkaline conditions (150 ml of 1 M NaOH). Xylan was first solubilized and a clear solution obtained. The vessel was closed and air in the vessel was replaced by nitrogen. The solution was incubated at room temperature overnight. After this the closed vessel was incubated at 150° C. for 2 h and cooled with cold water.

The solution was removed from the vessel and 7.5 ml of glycerol was added. The solution was neutralized by concentrated formic acid to pH 7. 150 ml of methanol was added dropwise with continuous stirring and the precipitate formed was removed by centrifugation. The precipitate formed was washed first with ethanol/water (1:1, 150 ml) and then with methanol (150 ml). The precipitate was dried at room temperature. The weight of the dry precipitate was 6.31 g (84% of the original xylan)

To analyse the xylan prepared, a small sample was ground manually and hydrolyzed by xylanase (pI 9) of $T.$ reesei at 40° C. for 24 h. The xylan concentration in the hydrolysis was 10 g/l, enzyme dosage 10000 nkat/g xylan and the buffer was 50 mM sodium acetate, pH 5.0. After the hydrolysis the sample was centrifuged, boiled and lyophilized. The lyophilizate was analysed by NMR. The sugar constituents of the hydrolysate were:

| | |
|---|---|
| xylose units | 95% |
| hexenuronic acid | 4.1% (bound to xylose units) |
| unidentified | 0.9% |

Example 3
Detection of Hexenuronidase Activity.

Hexenuronidase activity was detected by thin layer chromatography using the following procedure:

20 µl of enzyme sample was incubated with 20 µl of the hexenuronidase substrate (purified hexenuronoxylobiose. HexAX$_2$, prepared as described in Example 1, 0.2% solution in 50 mM Na-citrate, pH 5.3; or mixture of HexAX$_2$ and HexAX$_3$ obtained by a single gel filtration run) for 60 min at 50° C. Approximately 2 µl of the reaction mixture was applied as a small dot near (distance ca. 2 cm) the side of the chromatography plate (DC-Alufolien, Kieselgel 60, Merck Art, 5553). The plate was put sample side down in a glass chamber containing running solvent (50 vol-% acetone. 40% n-butanol and 10% distilled water, at a depth of 1.0–1.5 cm from the bottom). The running chamber was closed and the solvent front was allowed to rise approximately to the middle of the plate.

The xylobiose or xylotriose liberated in the hydrolysis reaction was detected by developing the plate as follows: The plate was air-dried for appr. 10 minutes. After this the plate was sprayed with the developer (10% H$_2$O, 10% conc. H$_2$SO$_4$, 80% ethanol and 0.2% 3.5-dihydroxytoluene, orcin: Merck 820933). The plate was dried (appr. 10 min on a paper) and developed by incubating it at 105–110° C. for 10 min. The xylobiose (and xylose, in the presence of β-xylosidase in the enzyme sample) formed could be detected as a coloured dot at the same distance from the starting line as the standard sugars (1–5 µl of 0.2% aqueous solution applied similarly to the hydrolysate). Thus the bond between hexenuronic acid and xylose was broken by hexenuronidase activity present in the enzyme sample, resulting in the release of free xylobiose.

Example 4
Quantification of Hexenuronidase Activity.

Hexenuronidase activity was quantified chromatographically using the following procedure:

400 µl of enzyme sample was incubated with 100 µl of the hexenuronidase substrate (hexenuronoxylobiose, HexAX$_2$, 0.2% solution in 50 mM Na-citrate, pH 5.3) for 10 min at 50° C., after which the reaction was terminated by boiling. The reaction mixture was analysed for xylobiose by h.p.l.c.-chromatography. The column used was an HC-40 (Hamilton Ca$^{2-}$ form). Milli-Q water was used as eluent at a flow rate of 0.5 ml min$^{-1}$. 1 mol of xylobiose liberated in the reaction corresponded to the simultaneous degradation of 1 mol of HexAX$_2$. On the basis of this correlation the activity removing hexenuronic acid groups from HexAX$_2$ (i.e. hexenuronidase activity) could be exactly quantified.

Example 5
Isolation of Microbial Strains Capable of Utilizing Oligomers Containing Hexenuronic Acid Samples of soil, discarded kraft pulp and unspecified solid material were collected from the storage area and inside the kraft pulp mill of Oy Sunila Ab at Kotka. Small subsamples (1–5 g) of the collected samples were suspended and vortexed in sterile saline and aliquots of 1 ml were transferred to 100 ml flasks containing 20 ml of a medium composed of solutions containing a mixture of HeGlcAX$_2$ and HeGlcAX$_2$ in 0.67 g l$^{-1}$ Yeast Nitrogen Base (YNB, Difco). The flasks were shaken for 3 days at 150 rpm and at 30° C. A loopful (appr. 10 µl) of the resulting dense microbial culture was then transferred to fresh medium of the same composition and the cultivations were repeated.

The final culture filtrates were centrifuged to remove the microbes and the clear centrifugates were diluted by a factor of 1:100 in distilled water. The optical absorbances of these dilutions were measured at 230 nm, at which wavelength the double bond of the hexenuronic acid had its maximum absorbance. These measurements indicated that the concentrations of oligomers containing hexenuronic acid groups had decreased almost to zero in all the culture filtrates (Table 4). The spectophotometry results were confirmed by oligosaccharide analysis using HPLC: HeGlcAX$_2$ and HeGlcAX$_3$ had completely disappeared from all the cultivation media (Table 4.) No other neutral or acidic mono- or oligosaccharides were detected in significant quantaties in either the medium or the culture filtrates.

Microscopical observation of the cultivations revealed that three contained predominantly bacteria (one proposed micrococcus and two different bacilli), whereas one of the cultures was contained predominantly a yeast.

TABLE 4

Removal of HexA-substituted xylo- ligosaccharides from culture filtrates initiated front suspensions of material samples from a pulp mill.

| Culture | pH | A$_{230}$ (diluted 1:100) | Residual oligosaccharides (mg l$^{-1}$) | | |
|---|---|---|---|---|---|
| | | | X$_2$ | HeGlcAX$_2$ | HeGlcAX$_3$ |
| Medium | 6.2 | 0.690 | 24 | 3600 | 5100 |
| 1 | 7.6 | 0.170 | 29 | 0 | 0 |
| 2 | 7.9 | 0.055 | 10 | 0 | 0 |
| 3 | 7.0 | 0.170 | 55 | 0 | 0 |
| 4 | 7.9 | 0.040 | (+) | 0 | 0 |

These results demonstrated that the cultures isolated by this kind of enrichment culture produced an enzyme capable of facilitating the metabolism of HeGlcAX$_2$ and HeGlcAX$_3$ in such a manner that the hexenuronic acid-containing xylooligosaccharide was completely utilized. Thus it is apparent that the cultures concerned produced hexenuronidase enzyme.

Example 6
Cultivation of Hexenuronidase Producing Cultures and Strains in Fermentor An isolate obtained as described in Example 5 (designated M4) was cultivated in a fermentor (800 ml working volume). An inoculum of 2.5 ml was prepared from a shake flask cultivation of 4 days on the medium described in Example 5. Cultivations were performed at 30° C. with agitation of 400 rpm and aeration of appr. 0.5 l/min. pH was controlled by HCl to be below 6.2. The cultivation medium contained 1.4 g/l HexAX$_3$. 6.2 g/l HexAX$_2$ (prepared as described in Example 1) and small amounts of methyl glucuronic acid, with Yeast Nitrogen Base (Difco) as a nitrogen source. The medium was sterilized at 120° C. for 20 min prior to cultivation. Cell count was monitored by plating on nutrient agar and consumption of oligomers containing hexenuronic acid by absorbance at 230 nm. The data from the cultivation is presented in the following Table:

TABLE 5

Cultivation data

| Time (h.min) | pH | Dissolved O$_2$ (%) | Cell count (ml$^{-1}$) | A$_{230}$ dilution 1:100 |
|---|---|---|---|---|
| 0.00 | 6.1 | 100 | 1.4 × 10$^7$ | 790 |
| 22.22 | 6.1 | 100 | 3.7 × 10$^6$ | 950 |
| 28.27 | 6.2 | 96 | 7.6 × 10$^6$ | 880 |
| 45.45 | 6.2 | 92 | 2.0 × 10$^8$ | 870 |
| 70.00 | 5.9 | 15 | 8.3 × 10$^8$ | 640 |
| 76.10 | 5.1 | 6 | 6.2 × 10$^9$ | 260 |

Several other mixed cultures and e.g. the pure strains VTT-E-94549, VTT-E-94559 and VTT-E-85235 could be cultivated using corresponding conditions. Similarly, in these cultivations oligomers containing hexenuronic acid (monitored by A$_{230}$) were consumed and cell counts higher than 2.0×10$^9$ were obtained. In most cases, the growth could be further accelerated by using fed-batch cultivation in the fermentor.

The microorganisms VTT-E-94549, VTT-E-94559 and VTT-E-94549 were deposited with DSMZ-Deutsche Sammlung von Mikroorganismen und Zellkulturen GmbH of Mascheroder Weg 1b, D-38124 Braunschweig, Germany, on Nov. 25, 2003, under the Accession numbers DSM 16061, DSM 16062 and DSM 16060, respectively.

Example 7
Confirmation of Hexenuronidase Activity in an Enzyme Preparation

The collected microbial cells from a mixed culture M4 cultivated in a fermentor as described in Example 6 were suspended in 0.05 M sodium acetate buffer, pH 4.8 and sonicated together with glass beads 5 times 10 s at 0° C. Cell debris and other insoluble material was separated by centrifugation and the supernatant was diluted (1:2) with 0.05 M sodium acetate, pH 4.8. This solution was used as an enzyme sample. 1 volume of enzyme sample was mixed with 10 volumes of substrate solution purified by ion exchange and gel filtration as described in Example 1. The reaction mixture was incubated at 30° C. for 24 h, after which the sample and corresponding reference samples were analysed by HPLC (Dionex Corp.). The results (see Table below) indicated that the substrate was completely degraded during the incubation, with formation of xylobiose and xylotriose. Thus the enzyme preparation obtained from culture M4 contained unquestionable hexenuronidase activity.

TABLE 6

Hexenuronidase activity of an enzyme preparation

| Sample | xylobiose (mg/l) | Xylotriose (mg/l) | HexAX$_2$ (mg/l) | HexAX$_3$ (mg/l) |
|---|---|---|---|---|
| Substrate without added sample | 0 | 0 | 330 | 180 |
| Enzyme sample | 0 | 0 | 0 | 0 |
| Substrate incubated with the sample | 82 | 180 | 30 | 0 |

The hexenuronidase activity of the enzyme sample described above can be separated from the other components of the mixture by conventional chromatographic methods, especially ion exchange chromatography, hydrophobic interaction chromatography, gel filtration, chromatofocusing and affinity chromatography.

Example 8
Improvement of Colour Reversion Properties by Removal of Hexenuronic Acids from Pulp Pine pulp (kappa number 25.9) was cooked in the laboratory using conventional methods. The characteristics of the pulp are presented in the following Table:

TABLE 7

Pulp characteristics

|  | Pine kraft pulp |
|---|---|
| Kappa number | 25.9 |
| Viscosity (dm$^3$/kg) | 1170 |
| Cellulose (% of dry weight) | 78 |
| Xylan (% of d.w.) | 11 |
| Glucomannan (% of d.w.) | 7.3 |
| Klason lignin and acid soluble lignin (% of d.w.) | 3.6 |
| Extractives (% of d.w.) | 0.1 |

The pulp was bleached in the laboratory using an OQP-sequence. The conditions in the Q-stage were: 4% consistency, pH 5.4, 0.2% EDTA and duration 1 h. The P-stage was carried out at 10% consistency at 90° C. and pH 11.5 with 2.5% H$_2$O$_2$ and 0.8% NaOH. The duration of the P-stage was 4 h.

After bleaching the pulp was treated with purified xylanase (pI 9) from *T. reesei*. The enzyme treatment (5000 nkat/g pulp) was carried out at 5% consistency at 45° C. for 24 h. The reference pulp was treated similarly but without enzyme addition. Handsheets were prepared after enzyme treatment according to SCAN C-11 (P3:75). The pulp (2 g dry weight) was suspended in 500 ml of water containing 10 mg/l EDTA and disintegrated for 3 min. The sheets were pressed for 1 min at 1.2 kbar and air dried for two hours in the dark at constant temperature and relative humidity before the brightness measurement and ageing treatment.

The contents of carboxylic groups in the untreated and xylanase-treated pulps were analysed by conductometric titration. The components removed in the xylanase treatment were analyzed by enzymatic hydrolysis of solubilized oligomers followed by HPLC-analysis as described by Tenkanen et al. (1995).

Accelerated ageing of handsheets was carried out in a climate chamber with relative humidity of 80% at 80° C. for 72 hours. The brightness values were measured before and after the ageing and pc-values were calculated according to Gierz (1945). The results from the enzyme treatment and from the ageing experiments of enzyme-treated and non-treated (reference) pulps are given in the following Table:

TABLE 8

Brightness stability of enzyme treated and non-treated pulps

|  | Pine kraft pulp |
|---|---|
| Carboxylic acids removed by enzyme treatment (% of dry weight) | |
| hexenuronic acid [a] | 0.17 |
| methyl glucuronic acid | 0.02 |
| Carboxylic acid content (mmol/kg dry pulp) [b] | |
| before enzyme treatment | 92 |
| after enzyme treatment | 72 |
| pc-value | |
| before enzyme treatment | 30.0 |
| after enzyme treatment | 21.6 |
| Decrease in pc-value | 28% |

[a] value for hexenuronic acid calculated from the amounts of oligomers containing hexenuronic acid
[b] determined by conductometric titration Removal of hexenuronic acid, in this case combined to partial removal of pulp xylan, resulted in a remarkable decrease in the pc-value. This indicates that the colour reversion properties of the pulp were clearly improved. It must be noted that corresponding enzyme treatment of pulps which do not contain hexenuronic acid groups has not given the effect demonstrated in this example. Thus the marked improvement in brightness stability of the pulp was obtained by removal of hexenuronic acid groups.

References

Giertz, H. W., Svensk Papperstidn. 48:13.3 17.
Tenkanen, M., Hausalo, T., Siika-aho, M., Buchert J. and Viikari, L. ISPWC Ext. Abstract, Wien 12–15 Jun. 1995.

What is claimed is:

1. A method for modifying a xylan-containing carbohydrate substrate having hexenuronic acid groups attached to the xylan, characterized in that at least a part of hexenuronic acid groups of the xylan-containing carbohydrate substrate is selectively removed from the xylan without affecting the chemical structure of the remaining part of the xylan-containing carbohydrate substrate.

2. The method according to claim 1, wherein the the hexenuronic acid groups are removed by contacting the xylan-containing carbohydrate substrate with an enzyme preparation having an essential hexenuronidase activity.

3. The method according to claim 2, wherein the xylan-containing carbohydrate substrate is contacted with a hexenuronidase preparation containing only minor amounts, if any, of hemicellulases.

4. The method according to claim 2 or 3, wherein the hexenuronidase preparation essentially comprises the cultivation medium or an intracellular extract of a hexenuronidase-producing microorganism strain.

5. The method according to claim 2, wherein the enzyme preparation contains glucuronidase activity in addition to hexenuronidase activity.

6. The method according to claim 2, wherein the xylan-containing carbohydrate substrate is first treated with an enzyme preparation having an essential hexenuronidase and optionally glucuronidase activity and subsequently contacted with an enzyme preparation having a hemicellulase, cellulase and/or ligninase activity.

7. The method according to claim 4 wherein the hexenuronidase preparation is derived from a genetically modified strain containing the gene coding for hexenuronidase.

8. The method according to claim 1, wherein the hexenuronic acid groups of the xylan-containing carbohydrate substrate are removed from the xylan in order to decrease the amount of metals in the xylan-containing carbohydrate substrate.

9. The method according to claim 1, wherein the hexenuronic acid groups are removed from the xylan in order to enhance chlorine-free bleaching of the xylan-containing carbohydrate substrate using, in particular, oxygen or peroxide.

10. The method according to claim 1, wherein the hexenuronic acid groups are removed from the xylan in order to reduce the colour reversion of the xylan-containing carbohydrate substrate.

11. The method according to claim 1, wherein the hexenuronic acid groups are removed from the xylan in order to improve the paper technical properties of the xylan-containing carbohydrate substrate.

12. The method according to claim 1, wherein the xylan-containing carbohydrate substrate is treated simultaneously with an enzyme preparation having hexenuronidase activity and an enzyme preparation having hemicellulase, cellulase and/or lignin modifying activity.

13. The method according to claim 1, wherein the xylan-containing carbohydrate substrate to be treated has been pulped by the conventional kraft process or by an extended cooking method.

14. The method according to claim 1, 12 or 13, wherein the xylan-containing carbohydrate substrate is treated with the enzyme preparation in order to enhance the action of hemicellulase, cellulase or ligninase, on the pulp.

* * * * *